United States Patent [19]

Gersten et al.

[11] Patent Number: 4,863,260
[45] Date of Patent: Sep. 5, 1989

[54] SYSTEM FOR TOPOGRAPHICAL MODELING OF ANATOMICAL SURFACES

[75] Inventors: Martin Gersten, Brooklyn, N.Y.; Richard J. Mammone, North Brunswick, N.J.; Joseph L. Zelvin, Larchmont, N.Y.

[73] Assignee: Computed Anatomy Inc., New York, N.Y.

[21] Appl. No.: 289,515

[22] Filed: Dec. 27, 1988

Related U.S. Application Data

[63] Continuation of Ser. No. 117,020, Nov. 4, 1987, abandoned.

[51] Int. Cl.$^4$ .............................................. A61B 3/10
[52] U.S. Cl. .................................... 351/212; 351/221; 351/246
[58] Field of Search ................ 351/206, 221, 212, 246

[56] References Cited

U.S. PATENT DOCUMENTS 3,797,921  3/1974  Kilmer et al. ...................... 351/206
4,662,730  5/1987  Outwater et al. .................. 351/212
4,685,140  8/1987  Mount, II .......................... 351/212

OTHER PUBLICATIONS

"Planar Reflected Imagery in Photokeratoscopy", *Journal of the Optical Society of America*, S. Wittenberg & W. Ludlam, vol. 60, No. 7, Jul. 1970, pp. 981–985.
"Corneal Topography: A Clinical Model", *Opthial. Physiol. Opt.*, M. Guillon, D. Lydon & C. Wilson, vol. 6, No. 1, pp. 47–56, 1986.
"Computer-Assisted Corneal Topography", *Investigative Ophthalmology & Visual Science*, S. Klyce, vol. 15, Dec. 1984, pp. 1426–1433.
"Method for Calculation of Corneal Profile and Power Distribution", *Arch Opthalmol*, J. Doss, R. Hutson, J. J. Rowsey, D. R. Brown, vol. 99, Jul. 1981, pp. 1261–1265.

*Primary Examiner*—Rodney B. Bovernick
*Assistant Examiner*—P. M. Dzierzynski
*Attorney, Agent, or Firm*—Howard R. Popper

[57] ABSTRACT

Apparatus and method for accurately quantifying the instantaneous radius curvature of a large plurality of points on the corneal surface is disclosed. A video image of the corneal surface accurately positioned at a predetermined point on the optic axis of measurement is obtained. The predetermined point is defined by intersecting low power laser beams. The video image is radially scanned from an original position at point defined by the intersection of the visual axis with corneal surface. Accurate measurements of the two-dimensional image radii of a plurality of illuminated mires reflective upon the corneal surface are made and corrected for camera distortions, quantization error and the different magnification occurring for different size corneas. The instrumentation is calibrated by using a plurality of mirror-like spheres of precisely known spherical radii.

13 Claims, 5 Drawing Sheets

FIG. 3
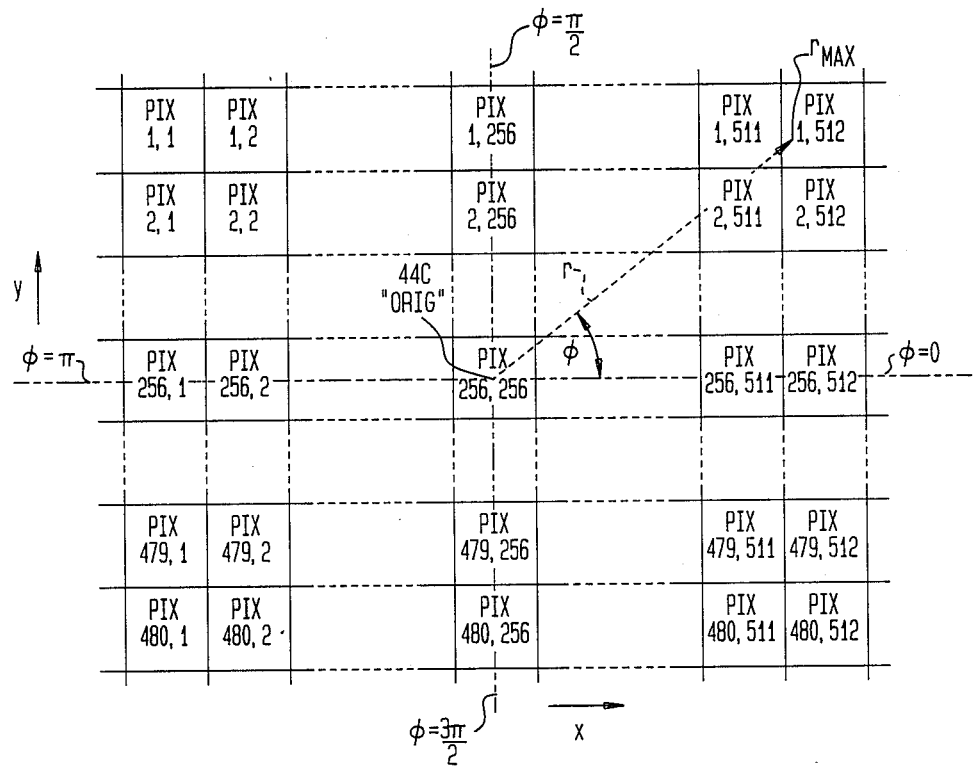
FIG. 4   REG (r, φ+Δ)
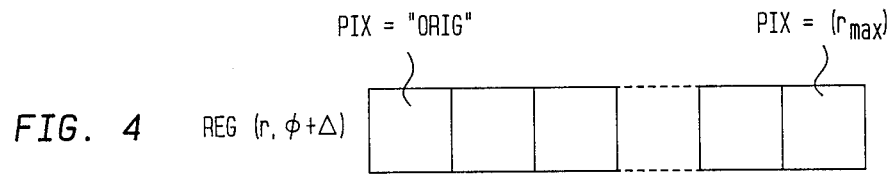
FIG. 5   REG (r, φ)

SYSTEM FOR TOPOGRAPHICAL MODELING OF ANATOMICAL SURFACES

This is a continuation of application Ser. No. 117,020, filed 11-04-1987 and now abandoned.

This invention relates to a system for mapping anatomical surfaces and, more particularly, to a system capable of providing quantitative graphic displays of corneal contours before and after eye surgery.

BACKGROUND OF THE INVENTION

A number of forms of eye surgery including lamellar corneal surgery, keratomileusis, epikeratophakia, cataract surgery, penetrating corneal transplantation as well as radial keratotomy involve a consideration of corneal surface topography. In radial keratotomy, for example, a number of cuts are made in the cornea to correct refraction so that images fall closer to the retina, if not upon it. It has been reported that after radial keratotomy "about 55 percent of the patients function without glasses and the remaining 45 percent have some degree of improvement". Origination of the technique of radial keratotomy is generally credited to Dr. Svyatasklav Fyodorov of the Soviet Union who is reputed to have performed over 2,000 such operations.

While ophthalmic surgery is often successfully performed, the results obtained have been subject to variation occasioned by the particular operating "style" of the individual surgeon which dictates the number, location and depth of incision. Elements of subjective judgment are paramount. It would be useful to provide a device that could assist the surgeon in more quantitatively assessing pre-operative and post-operative corneal contours.

GENERAL SUMMARY OF THE INVENTION

In accordance with the principles of the present invention, the surface geometries of a human cornea, and, particularly, the various dioptric powers of refraction existing at different points of its surface, are quantitatively described by processing the data contained in a video image of the cornea upon which has been reflected a predetermined illuminated pattern, such as that produced by a plurality of illuminated, calibrated concentric rings or mires. Twenty, thirty or more illuminated rings may be caused to be reflected on the cornea using the illuminated ring projection device described in the co-pending patent application entitled "Illuminated Ring Projecting Device", Ser. No. 902,610, filed Sept. 2, 1986. In accordance with one aspect of our invention, this device is modified so that a two-dimensional video image of the ring pattern appearing on the cornea may be acquired when the apex of the cornea is at a precisely known location along the optical axis. The ring pattern may then be correlated with the pattern produced upon a similarly positioned standard spherical surface such as that of a shiny steel ball of known diameter. The correlation provides sufficient data to quantitatively display the various diopters of refraction exhibited at different points of the cornea. In the illustrative embodiment the corneal apex is located by intersecting laser beams introduced through apertures in the cone of the aforementioned projection device.

In accordance with a further aspect of our invention, the coordinates of pixels in the pattern of illuminated rings appearing on the cornea (or on the reference sphere) are acquired by radially scanning the two-dimensional video image orthogonally to the illuminated pattern. The pixels in the pattern of each mire encountered on a radial scan are distinguished from other pixels by convolving each of the pixel illumination values by the coefficients of an empirically formulated matched digital filter. Outputs from the matched filters exceeding a predetermined threshhold identify pixels corresponding to the center of the "thickness" of each of the intercepted mires.

Since even a normal human cornea will not be perfectly spherical, the illuminated rings will generally be reflected from the corneal surface as a pattern of shapes variously distorted from the circular. Further, image artifacts, such as specular glare and eyelash reflection may interfere with the pattern reflected from the cornea. In accordance with one aspect of our invention the acquired video image is processed to obviate the effects of such artifacts and of distorting effects that may be introduced by the optical or electronic apparatus as well as those arising from mirror magnification at the corneal surface. The data pertaining to the coordinates of points in the two-dimensional video image is processed to define a three-dimensional corneal surface yielding the equivalent spherical radius of curvature (or dioptric power) for each of the acquired points.

BRIEF DESCRIPTION OF THE DRAWINGS

The foregoing objects and features of our invention may become more apparent from the following general description when read together with the drawing, in which:

FIG. 3 depicts the frame store containing the video data arranged for radial scanning from an origin correlated to the corneal apex;

FIGS. 4 and 5 depict the "ring hit" registers for storing pixel amplitudes read along different radii of the pixel data map;

FIG. 6-1 shows a top view of the illuminated ring apparatus of FIG. 1 which employs laser beams to achieve accurate axial positioning of the corneal apex;

FIG. 6-2 is a frontal view of an illustrative one of the plurality of rings reflected on a corneal surface positioned in the apparatus of FIG. 6-1;

GENERAL DESCRIPTION

Figure 1:
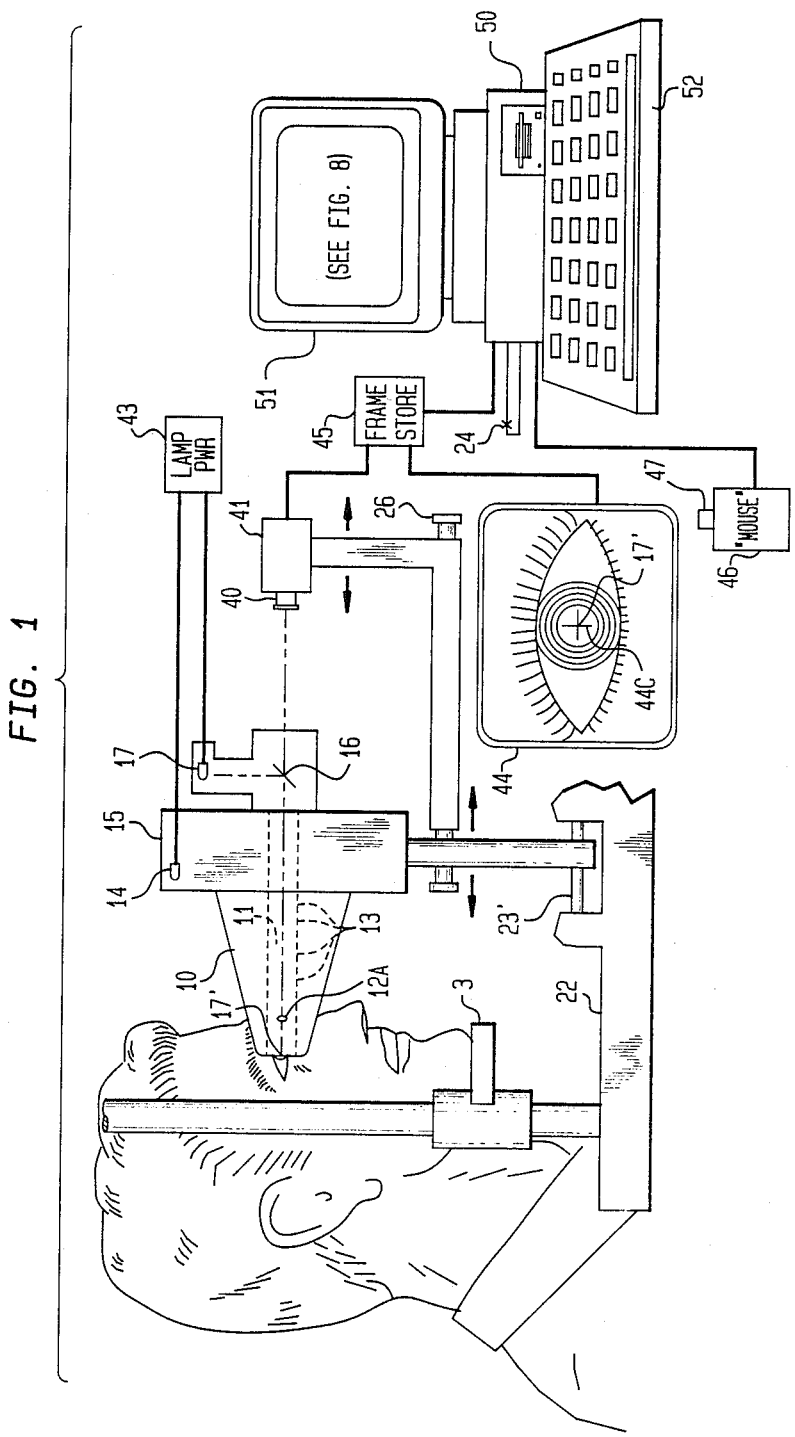
FIG. 1 schematically shows the ring projection, video monitoring and image processing combination of our invention.

Referring to FIG. 1, a schematic layout of the apparatus for practicing the method of our invention is shown. The apparatus causes the plurality of coaxially disposed illuminated rings 13 inside cylinder 11 and internally tapered disc 18F of keratoscope assembly 10, 15 to be reflected upon the cornea of the patient's eye. The keratoscope cone and light box assembly 10, 15 may be of the general type described in the above-mentioned co-pending application or preferably may be modified as hereinafter described. The patient's chin rests on chin rest 3 and the patient is asked to concentrate, i.e., to focus upon, the (virtual) image of the fixation light 17 appearing on pellicle 16. The keratoscope assembly 10, 15 is positioned so that its optical axis is aligned with the reflection 17′ of the fixation spot appearing upon the patient's cornea.

In addition to the keratoscope cone assembly 10 and lamp housing 15, the illustrative apparatus comprises a video camera 41, frame store 45 and microcomputer 50 for acquiring storing and processing a two-dimensional image of the illuminated rings. Video monitor 44 displays the camera image in either the form initially acquired by the camera or as enhanced by the computer processing hereinafter to be described. Computer monitor 51 displays the "menu" for guiding the operator through the processing steps as well as the graphics output of the computer process. Advantageously, the graphics output may be superimposed on enhanced image displayed by monitor 51. A keyboard 52 and advantageously a "mouse" 46 may be used for positioning a cursor 44C on the displayed image.

Figure 2:
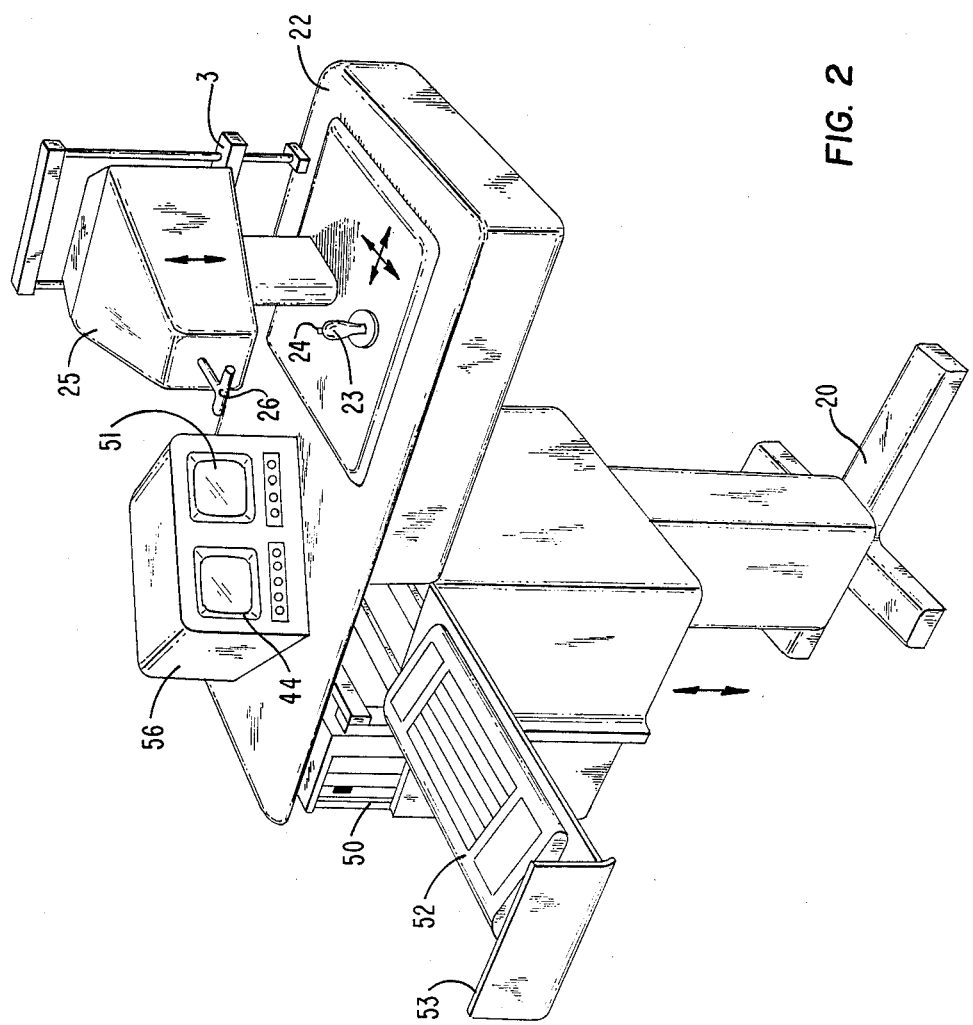
FIG. 2 shows a practical embodiment of the apparatus of FIG. 1.

FIG. 2 shows, in pictorial form, a practical embodiment of the apparatus of FIG. 1 wherein the table 22, supported on pedestal 20, carries cone and light box assembly 10, 15, as well as video camera 41 all contained within optical head 25. Raising and lowering of table 22 to accommodate different patients is provided by a separate control (not shown). Optical head 25 is movably mounted on table 22 relative to chin rest 3. To provide for coarse adjustment of the location of housing 25 forward and backward and side to side with respect to the position of chin rest 3, lever 23 is manipulated. "Joystick" lever 23 may advantageously actuate a three-motion mechanism such as that disclosed in U.S. Pat. No. 3,463,579 which describes an adjusting mechanism for a well-known form of slit lamp apparatus. As an alternative to the completely mechanical "joystick", however, lever 23 may be equipped with auxiliary rotational motion sensing pick-ups (not shown) so that when rotated in one direction a signal will be generated to raise optical head 25 with respect to table 22 and chin rest 3 and in the other to lower the optical head. Another lever 26 is associated with optical head 25 to provide for fore and aft movement of the keratometer and camera along the optical axis.

A pushbutton 24 is conveniently located in the top of lever 23 so that the operator may send a signal to computer 50 to transfer the video image acquired by camera 41, as displayed on video monitor 44, to frame store 45. Frame store 45 may be mounted in one of the expansion card slots of computer 50. In the illustrative embodiment, computer 50 was an IBM-AT compatible computer manufactured by PC Limited employing a Matrox SM 640 graphics card. Frame store 45 was model FG100-AT manufactured by Imaging Technology, Inc., Wobourn, Mass. The frame store acquires each pixel in the video image as a 6-bit digital pattern representing the amplitude of local illumination.

Figures 1, 2, 6:
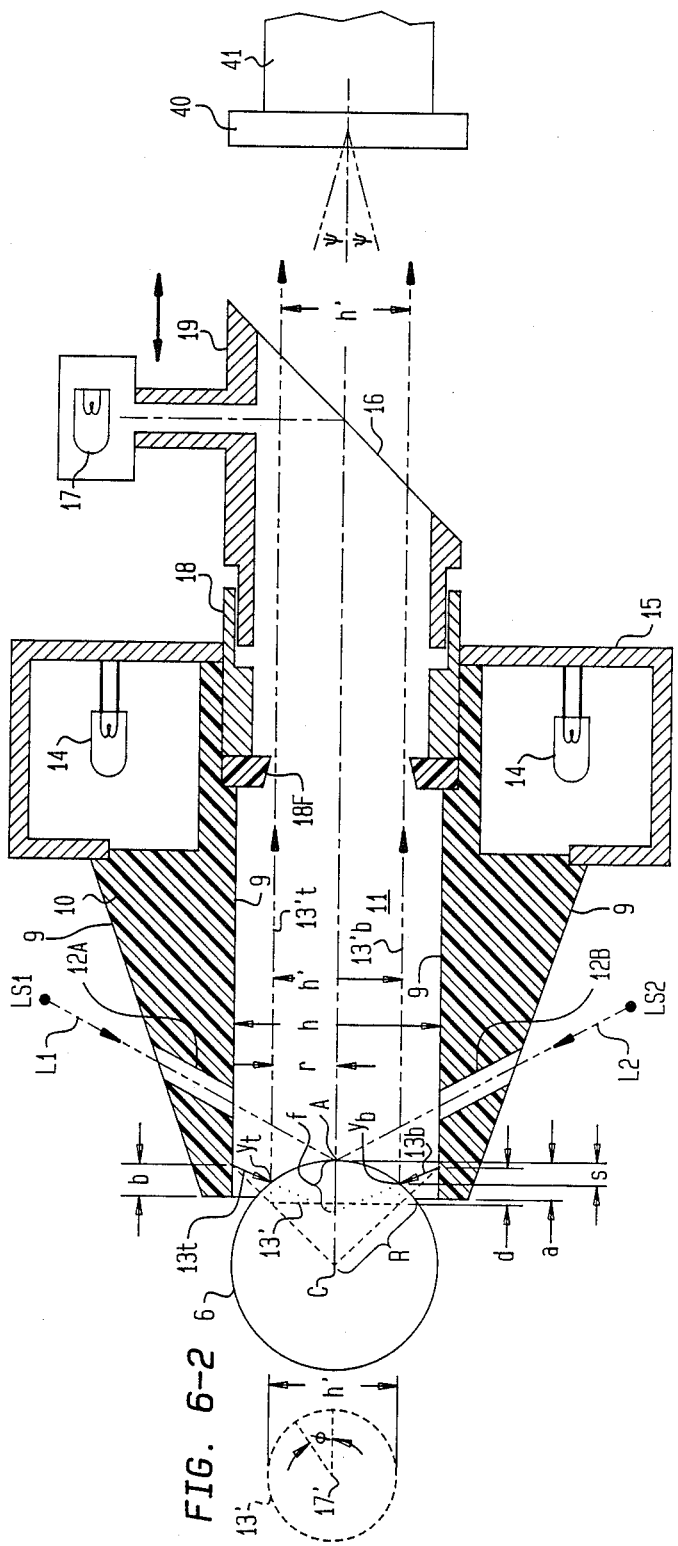
Figure 7:
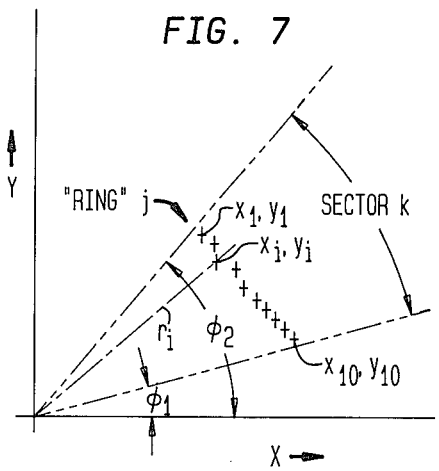
FIG. 7 schematically illustrates a collection of data points acquired by scanning a sector of the pixel data map.
Figure 8:
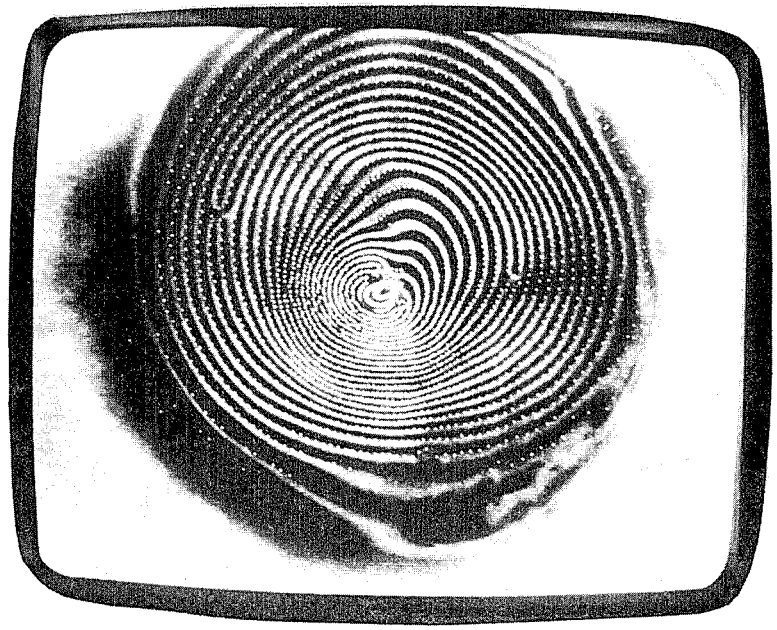
FIG. 8 is a photograph of the actual video image of the "ring hit" data acquired by our processing method superimposed upon the acquired video image of the illuminated rings appearing on the cornea of a patient exhibiting keratoconis.

Referring now to FIG. 6-1, a top, cross-sectional view is shown of the cone and light box assembly 10,15 of our co-pending invention as modified in accordance with the principles of our present invention. A pair of apertures 12A,12B are bored through cone 10 at an angle, illustratively 60 degrees, to its central axis. A pair of low power helium-neon lasers LS1,LS2 are optically aligned with the aperture bores to provide beams L1,L2 that intersect within the central corridor 11 of the cone at a point A located at a distance a from its left-hand open end. Lasers LS1,LS2 are advantageously 2-milliwatt devices and may be conveniently located anywhere within housing 25 by the use of mirrors (not shown). To provide for accurate location of the patient's cornea, the beams L1,L2 converge at point A on the optic axis.

An additional modification to the structure disclosed in our above-mentioned co-pending patent application includes an interior plastic disc 18F, a metal extension tube 18, and a slidably mounted fixation light assembly 19 carrying the fixation light 17 and pellicle 16. Disc 18F may advantageously be provided with an internally tapering surface projecting part way into central corridor 11. An opaque coating 9 lines the central corridor 11 including the inside surfaces of cylinder 18, disc 18F, extension tube 18 and assembly 19. The opaque coating is removed at predetermined spaced intervals in such a manner as to cause the light from lamps 14 to provide a series of 20 to 30 or more evenly spaced illuminated rings 13 to appear on the spherical shiny surface 6 of a reference sphere of known diameter. Coating 9 may also be partially removed from tapered portion 18F to permit light from light box lamps 14 to illuminate a portion of its tapered surface and thereby provide an additional mire (not shown) to be reflected upon sphere 6. In addition, some of the coating on the left face of disc 18F may be selectively removed to reveal one or more additional mires 13. In the illustrative embodiment, the smaller diameter of the tapered portion of disc 18F was 0.510″ and its larger diameter was 0.582. The left-facing surface of disc was located 2.9″ from the open end of cone 10 while the coating on this surface was machined away to reveal a ring having a minor diameter of 0.764″ and a major diameter of 0.856″.

The eye of a patient or, as shown in FIG. 6-1, its schematic representation by the mirror-finished ball 6 having a radius R of 7.848 mm (equivalent to a diopter cornea) is positioned at the left-hand end of passageway 11. Lever 23 (FIG. 1) is manipulated so that the cone is advanced toward the patient's eye (i.e., sphere 6). The patient is asked to focus on a fixation spot provided by the reflection of fixation light 17 appearing on pellicle 16 mounted at the right-hand end of fixation light assembly 19.

When the target cornea, or the calibrating ball 6 (FIG. 6-1) is too far from the left-hand end of cone 10, the intersecting beams produce two visible spots. As lever 26 is advanced to bring cone 10 closer, the spots merge and diverge again once point A is passed. The point of exact focus, point A, is located a distance a, in the illustrative embodiment, 3.2 mm from the end of cone 10. When laser beams L1,L2 form a single spot on sphere 6 at point A, the reflection 17′ (FIG. 6-2) of the fixation spot on the patient's eye (sphere 6) is also at point A. It may be noted that in patients suffering from keratoconus the visual axis may not correspond to the corneal apex.

Pushbutton 24 (FIG. 1) may now be actuated to switch off lasers LS1, LS2 and to switch lamps 14 inside light box 15 to brightness to back-light each of the thirty rings 13 cut into the opaque lining 9 of passageway 11. Lamps 14 are advantageously 14 volt quartz halogen bulbs which receive their power from source 12 under control of computer 50.

For the sake of clarity, the incident and reflected ray 13t, 13′t from the top and the incident and reflected ray 13b, 13′b from the bottom of only one of rings or mires 13 located toward the left-hand end of passageway 11 is shown in FIG. 6-1. As shown, inter alia, in the article "Keratometry" by Janet Stone in the book *Contact Lens Practice*, a ray incident upon a spherical mirror aimed at the focus f' will be reflected parallel to the optic axis and will produce a virtual image which appears to lie beneath the surface of the sphere. The image point on the plane of the virtual image may be located by projecting the reflected ray parallel to the optic axis until it intersects a line drawn from the object point to the center of the sphere. The radius of curvature of the sphere is is given by the relationship:

$$R = 2dh'/h, \quad (1)$$

where d is the distance measured along the optic axis between a point on the plane of (object) ring 13 and its image point on the plane of image 13'; h is the diameter of the object ring 13' and h, is the apparent height (diameter) of the ring image. The image of mire 13 on sphere 6 is shown as the dashed line 13' in FIG. 6-1 and as the dashed circle 13' in FIG. 6-2.

While the above formula is of interest in focusing a camera to acquire a "picture" of the virtual image ring 13' when the camera is located at a much greater distance from the object than the object's diameter, camera 41 in the illustrative embodiment of FIG. 1 is located quite close to the object. In addition, formula (1) assumes that the area of interest on the surface of the spherical mirror is small compared with the radius of the surface; such mirrors are said to have a small aperture. In contrast, the plurality of mires caused to be reflected upon sphere 6 in our apparatus extend over a large surface of the sphere.

When the camera is located close to the object, as is camera 41 in FIG. 1, the virtual image acquired by the camera will appear to be "magnified" larger or smaller compared to the image predicted from the backward extension of the reflected ray parallel to the optic axis. See, for example, FIG. 1 of the article entitled "Planar Reflected Imagery in Photokeratoscoy" by S. Wittenberg and W. M. Ludlam, "*Journal of the Optical Society of America*," Vol. 60, No. 7, July 1970, pp. 981–5. Accordingly, the length of the observed image radius, r, as obtained by the above formula (1) must be corrected. We have discovered that by positioning the apical surface of a reference sphere of known spherical radius, R, just touching point A in FIG. 6-1, and measuring the radius r in the acquired image we may ascertain certain correction factors that will enable us to accurately determine the radius, $R_2$, of a similarly placed unknown sphere by measuring its image radius $r_2$.

Assume that a reference sphere of accurately known spherical radius R, illustratively 7.8 mm, is positioned on the optic axis with its apical surface just touching point A. Neglecting for the moment the fact that the ray picked up by camera 41 is the ray which is at an angle ψ to the optic axis rather than the parallel ray, and assuming that it is the parallel ray, the geometrical relationship among the spherical radius R of the known standard sphere, the radius r of the virtual image 13' of object mire 13 and the sagittal depth s of the plane perpendicular to the optic axis intersecting the sphere at the point of incidence and reflection is given by:

$$(R-s)^w + R^2 = R^2, \text{ or} \quad (2)$$

$$R = 1/2 \ (R^2/s + s). \quad (3)$$

Now if the first reference sphere R is replaced in FIG. 6-1 by a second reference sphere of radius, $R_2$, equation (3) becomes:

$$R_2 = \tfrac{1}{2}\left( \frac{r_2^2}{s_2} + s_2 \right). \quad (4)$$

From the ratio of the radius of the image mire 13' of the second reference sphere to that of the corresponding image mire of the first reference sphere we may define a constant of proportionality, k, such that:

$$r^2 = kr, \text{ and } s_2 = ks. \quad (5)$$

Once the constant of proportionality is known, equation (3) may be rewritten as:

$$R^2 = \tfrac{1}{2} \ (kr)^2/ks + ks, \quad (6) \text{ or}$$

$$R^2 = k/2 \ (r^2/s + s). \quad (7)$$

Noting from (3) that $$\tfrac{1}{2}\left( \frac{r^2}{s} + s \right) = R,$$

we have:

$$R^2 = kR, \quad (8)$$

i.e., the spherical radius of the second sphere may be calculated from that of the first by the constant of proportionality factor, k, determined from the ratio of the two-dimensional radii $r_2/r$. Note, however, that the constant of proportionality k may be different for each of the ring mires. Accordingly, where, as in the illustrated embodiment, 32 mires are employed, there will be 32 distinct values of k.

In terms of the observed two-dimensional image radius, $r_2$, the corresponding spherical radius, $R_2$, of any similarly positioned sphere equation (6) may be rewritten as:

$$R^2 = Gr_2, \quad (9)$$

$$R_2 = Gr_2, \text{ where } G = \frac{r}{2s} + \frac{s}{2} r. \quad (9)$$

Since G is constant based on the two-dimensional radius r of the reference sphere, equation (9) states that we can calculate the spherical radius $R_2$ of an unknown sphere from a measure of its observed two dimensional image radius, $r_2$, by applying the proportionality factor G.

It may be noted that our proportionality factor G is roughly comparable to the constants arising from the apparatus configuration discussed in the remainder of the cited article by Janet Stone, supra, with the exception that Stone's calculations presume that all of the spheres will have the centers at the same point. The apparatus of our FIG. 6-1, however, is based on having all of the different spheres' apices at the same point, A which, in the case of a cornea, is the point at which the visual axis intersects the corneal surface.

Having set forth the foundation for determining the spherical radii corresponding to points on the image whose two-dimensional radii have been determined, it is appropriate now to describe the process of acquiring image data and of correcting the data to obtain an accurate measurement of the object giving rise to the image.

The actuation of pushbutton 24 allows the video image of the illuminated ring pattern appearing on sphere 6, as acquired by video camera 41, to be entered into frame store 45. The acquired image is simultaneously displayed on video monitor 44 so that the operator may position crosshairs 44C at the point from which the stored image will be scanned for the computerized analysis that will report the radius of curvature R at each of several thousand points on the image. Crosshairs 44C are positioned by manipulating either "mouse" 46 or the numeric keypad 47 of keyboard 52 and button 47 is then pushed to begin scanning. The location of the fixation spot is a preferred point from which to begin scanning of the data in the frame store since that location will coincide with the patient's visual axis, at least for patients whose macula and fovea are normal.

The pixel positions in frame store 45 containing illumination data, i.e., the six-bit values representing light amplitude, are depicted in FIG. 3. Scanning of the frame store pixel values is done radially, beginning at a predetermined "azimuth" angle $\phi$ such as $\phi=0$. At a particular azimuth angle $\phi$, the "instantaneous radius r" at which pixel positions exists in the frame store are recorded together with the stored 6-bit illumination values. As is well-known, it is necessary to adjust the x,y coordinate values of frame store pixel positions both for the particular aspect ratio of the monitor screen (width to height, illustratively, 4:3) and for the different number of pixels in the x and y directions (512,480). In addition, the pixel illumination values in the frame store may be averaged and each of the individual values replaced by the difference between it and the averaged value. The illumination values then encountered on a radial scan of the normalized stored values at a particular azimuth angle $\phi$ are recorded from $r_{min}$ at the fixation spot (corneal apex) to $r_{max}$ at the corneal limbus in a "ring hit" register, FIG. 5. In the illustrative embodiment where there are 31 mires, up to 31 such illumination values may be encountered at each azimuth of scanning.

A mire's image exhibits a finite thickness that may occupy 3 or more pixel positions. The inter-ring space (exhibiting lower illumination values) may occupy 4 to 12 pixel positions. To more accurately locate the pixel position corresponding to the center of the "thickness" of each of the intercepted mires, the 6-bit values in the ring hit register are copied into an accumulator register (not shown) and sequentially multiplied by the coefficients of an empirically formulated matched filter. This procedure, denominated "hipass ———filter radial vectors" is set out in the appendix. Multiplying by the impulse function and selecting products above a predetermined threshhold more sharply identifies a single pixel for each of the up to 32 mires intercepted on a radial scan.

As an alternative, or in addition to the steps of multiplying illumination values obtained from a single scan by the coefficients of the matched filter and then threshholding, as just described, the illumination values obtained on an adjacent radial scan at azimuth angle $\phi+\Delta$ may be entered into a second ring hit register as shown in FIG. 4. The contents of corresponding positions of the hit registers for successive radial scans may then be multiplied together and the resulting product truncated to replace the contents of the first ring hit register of FIG. 5. This procedure may be used to clarify the data as when artifacts cause illumination values to be missing at a given radius on adjacent scans. The scanning, multiplying and threshholding are repeated 255 times at uniform increments of azimuth angle $\phi$ to complete a table of approximately 255×32 polar coordinates of points on the illuminated rings.

It should be noted that with a finite number of pixels there will be some quantization error in measuring the radius to the center of thickness of each ring encountered on a radial scan. This error can be corrected to some extent by more accurately finding the center of the circular mire pattern, preferably of an inner one of the rings and then correcting all of the radii in the entire pattern. The radius offset is the square root of the sum of the squares of the average offset in each coordinate direction. Further, the azimuth angle for each of the 256 radial scans may be adjusted by the offset in angle computed by the arc tangent of the quotient of the average y coordinate offset and the average x coordinate offset.

Ideally, the "ring hit" coordinates of points on the same ring should all have the same radius coordinate, r, and differ from each other only by their azimuth coordinate, $\phi$. Thus data obtained using the calibrating sphere should provide 256 identical values of r for each ring. However, various distortions arising, for example, from the camera, the keratoscope target or the digital electronics cause the 256 values for the same ring to differ somewhat from a constant value. To correct for the effect of such distortions, sometimes hereafter to be referred to generically as camera distortions, a further table of 256×32 correction coefficients is constructed wherein each of the entries is of the form:

$$k_{(ind)} = r_{(avg)}/r_{(ind)}, \qquad (10)$$

where $r_{(avg)}$ is the average of the 256 recorded radii, and $r_{ind)}$ is the individual radii. With this table of coefficients each of the radius values recorded on scanning a patient's cornea may be corrected for camera distortion by the formula:

$$r_{(corr)} = r_{(meas)} * k_{(ind)}. \qquad (11)$$

Results obtained with an illustrative embodiment of the apparatus have proved to be repeatable to within +/−10 microns.

Having obtained a table of 32×256 values of $r_{(corr)}$ the corresponding values of spherical radii may be computed from equation (9). However, these values must be corrected for the different magnifications arising because our apparatus, as shown in FIG. 6-1, positions the apical surface of each sphere at point A, i.e., spheres of different spherical radius will have their centers at different locations on the optical axis. Our preferred method is to define a parameter, x, such that the magnification may be seen to vary solely as a function of the spherical radius. Thus, we may define:

$$x = \frac{R_2 - R_{ref}}{R_{ref}} \qquad (12)$$

where $R_2$ is the spherical radius as determined by the use of equation (9) and $R_{ref}$ is the accurately known spherical radius of a calibration standard sphere. A function, M(x), may now be defined to relate the magnification effect of a sphere of unknown spherical radius positioned at point A relative to the magnification effect of the reference sphere.

Allowing M(x) to be expressed as a Taylor series expanded about the origin, we have:

$$M(x) = 1 + a_1 x + a_2 x^2 + a_3 x^3 + \ldots \quad (13)$$

For a first order approximation, we may simplify equation (11) by disregarding all but the first two terms:

$$M(x) = 1 + a_1 x \quad (14)$$

The least-squares solution to equation (14) for $\Theta_1$ is obtained for a range of spherical radii likely to be encountered, e.g., 6.75 to 8.8 mm, equivalent to 50 to 38 diopter corneas. Advantageously, this solution may employ a simple matrix transformation since there is only a single unknown $\Theta_1$. Accordingly, the spherical radius obtained by the use of equation (9) needs to be corrected by the use of the following relationship:

$$R_{(cor)} = M(x) R_2 \quad (15)$$

In general terms, equation (15) expresses the proposition that the spherical radius of a small sphere should be corrected in the direction of making it smaller and that of a large sphere in the direction of making it larger to obviate the effects of the different positions of the spherical center occasioned by having their apice fixed at point A.

Having obtained the corrected spherical radius for each of the approximately 256×32 observed two dimensional radii, the next step in our method is to substitute the corresponding sagittal heights, s, into the well-known equation of the corneal profile based on the conical section as described by Guillon, Lydon and Wilson in the article entitled "Corneal Topography: Clinical Model" published in *Optial Physiol. Opt.* Vol. 6, No. 1 pp. 47–56, 1986. When the apical radius $R_0$ is positioned at the origin of a coordinate system whose ordinates are r and whose abscissas are s, the profile formula is:

$$r^2 = 2 R_0 s - p s^2, \quad (16)$$

where p is the shape factor of the family of conical sections. The shape factor indicates the degree of departure of the curve from the apical radius $R_0$. The curve is hyperbolic for value $p<0$; parabolic when $p=0$; spherical when $p=0$; oblate ellipsoidal when $0<p<1$ and prolate ellipsoidal when $p>1$.

It should be appreciated that while equation (16) is an equation in only the two unknowns $R_0$ and r, the data obtained by our process of radial scanning produces as many as 32 equations because there may be as many as 32 ring interception values, r, on each profile "scan". These 32 sets of equations are solved by using Gauss' least squares technique.

Having obtained the most accurate solution to equation (16) we know the exact corneal profile. The exact corneal profile may then be used, for example, to construct an "exact" contact lens. In addition, the curvature K at any point (s,r) on the profile may be determined from the relationship:

$$K = \frac{\frac{d^2 r}{d s^2}}{\left[1 + \left(\frac{d r}{d s}\right)^2\right]^{3/2}} \quad (17)$$

Substituting equation (16) into (17) gives the actual spherical radius (in millimeters):

$$K = \frac{R_0^2}{[r^2 + (R_0 - ps)]^{3/2}}. \quad (18)$$

The actual refraction at the point (s,r) is then given by multiplying equation (18) by the actual index of refraction of the cornea (1.376), minus the index of refraction of air, or:

$$D = 0.376 K, \quad (19)$$

where D is in diopters.

What has been described is illustrative of the principles of our invention. Numerous modifications may be made by those skilled in the art without, however, departing from the spirit and scope of our invention.

APPENDIX

```
program keratoscope_video_to_polar_ring_file;
                                {September 8, 1987 by Mart}
    {$I-,C+}
    const
        iphe_offset = 7;
        last_ring = 30;
    type
        ring_circ_data = array[0..lim] of real;
        corneal_file = array[0..final_ring] of ring_circ_data;
        corneal_ptr = corneal_file;
    begin
        get_filename_for_display(input_filename,photo_num,
        key);
            open_file_for_read(filename,filvar,error);
            begin
                get_6_bit_frame(fb0,filvar,key);
                find_center(auto_center);
                histogram_equalizer(tran,key);
                    hipass_filter_radial_vectors;
                    begin
                        starting_irad := radius_vact[start_ring-1];
                        identify_start_radii(starting_irad,starts);
                        correct_errors_in_start_radii(starts);
                        analyze_keratoscope_data(starts,tot_rings);
                        write_real_rings_to_disk(filename);
                        dispose(real_ring);
    end.
    procedure hipass_filter_radial_vectors;
    var
        i,iphe,irad,iang,j,threshold,offset0,pixel,k,accum: integer;
        rbuf,buf: array[start_rad..last_rad] of integer;
    const
        max_elem0 = 6;
    type
        filter0 = array[0..max_elem0] of integer;
    const
        impulse1{0}: filter0=(-7,-7,2,24,2,-7,-7);
    begin
        offset0 := max_elem0 div 2;
        for iphe := 0 to lim do
            begin
                for irad := start_rad to last_rad do
                    begin
                        read_low_polar_pixel(fb0,iphe,irad,rbuff[irad],
                        error);
                            if rbuf[irad] = hit_ring then
                                write_polar_pixel(fb0,iphe,irad,hit_ring-1);
                    end;
                fillchar(buf,2*(last_rad-start_rad+1),0);
                for irad := start_rad to last_rad-max_elem0 do
                    begin
                        accum := 0;
                        for k := 0 to max elem0 do
                            accum := accum + rbuf[irad+k] *
                            impulse1[k],
                        buf[irad+offset0] := accum;
                    end;
                for irad := start_rad+1 to last_rad − max_elem0 do
                    begin
                        case irad of
```

APPENDIX-continued

```
            0..20: threshold := {40} 40;
            21..63: threshold :={20} 20;
            64..255: threshold := {10} 10;
        end;
        if buf[irad]>threshold then
            if (buf[irad-1]>threshold) or
                (buf[irad+1]>threshold) then
                write_polar_pixel(fb0,iphe,irad,
                        hit_ring);
            end;
    end;
end;
program gen_refractive_powers;
                    { gen_diop.pas }
                {September 25, 1987 by
                                Mart.}
const
    actual_last_ring = 31;
type
    cal_array = [1..actual_last_ring] of real;
const
    min_rad = 3.0;
    iblock = 16;
    lim = 255;
    lim1 = 256;
    scale = 44.0;
    ref_ball_radius = 7.849;
    last_g_ring = 28;
    file_g = '/tables/g7848b.tab';
    file_e = '/tables/e7848a.tab';
type
    words = string[80];
    corneal_data = array[0..lim] of real;
    corneal_file = array[1..actual_last_ring] of corneal_data;
    corneal_ptr =   corneal_file;
var
    jphi,iring,last_ring: integer;
    rc: corneal_data;
    real_ring,ht,g,diop,mag_err: corneal_ptr;
    ring_fil,diop_fil,ht_fil,g_fil,e_fil: file;
    rad,mean_spherical_radius,mean_x,mean_y,aperiodicity_factor:
real;
    min_diop,max_diop,diopter,ring,x,y,adjusted_ring_radius:
real;
    input_filename: words;
    error: boolean;
    key: char;
begin
    get_processing_info(input_filename,last_ring);
    if (last_ring < 1) then
        exit;
    open_files(input_filename,g_fil,ring_fil,diop_fil,ht_fil,error)
    if not error then
        begin
            if last_ring > last_g_ring then
                last_ring := last_g_ring;
            min_diop := 1000.0;
            max_diop := 0.0;
            new(real_ring);
            new(diop);
            new(ht);
            new(g);
            new(mag_err);
            key :=' ';
            assign(e_fil,file_e);
            reset(e_fil);
            for iring := 1 to actual_last_ring do
                blockread(e_fil,mag_err [iring],iblock);
            close(e_fil);
            load_input_files(ring_fil,g_fil);
            iring := 0;
            seek(ring_fil,0);
            repeat
                iring := iring + 1;
                check_for_outliers(real_ring [iring]);
                for jphi := 0 to lim do
                    real_ring [iring][jphi] := real_ring [iring][jphi]
                                mag_err [iring] jphi];
                interpolate_through_holes(real_ring [iring]);
                smooth_circumference(real_ring [iring],iring);
                if iring = 1 then
                    mean_center(real_ring [iring],mean_x,mean_y);
                { Compute first pass at mean spherical radius }
                for jphi := 0 to lim do
                    begin
                        ring := real_ring [iring][jphi];
                        polar_to_rect_real(jphi,ring,x,y);
                        real_ring [iring][jphi] := sqrt(sqr(x-mean_x) +
sqr(y-mean_y));
                        rc[jphi] := g [iring][jphi] *
real_ring [iring][jphi];
                    end;
                { For this ring only }
                mean_radius(rc,mean_spherical_radius);
                aperiodicity_factor := 1.0 / (1.0 + 0.22 *
((ref_ball_radius/mean_spherical_radius)-1,0)));
                { Compute final instantaneous spherical radius and
                    final instantaneous height }
                for jphl := 0 to lim do
                    begin
                        { Correct spherical radius for aperiodicity }
                        rc[jphi] := rc[jphi] * aperiodicity_factor;
                        ht [iring][jphi] := rc[jphi]
sqrt(sqr(rc[jphi]) –
                                sqr(real_ring [iring][jphi]
/ scale));
                        diop [iring][jphi] := 337.5 / rc[jphi];
                        if diop [iring][jphi] > max_diop then
                            max_diop := diop [iring][jphi];
                        if diop [iring][jphi] < min_diop then
                            min_diop := diop [iring][jphi];
                    end;
                writexy(12,12,'');
                write(' Ring #',iring:3,
                        ' mean power = ',337.5
mean_spherical_radius:5:2);
                if keypressed then
                    read(kbd,key);
            until (iring = last_ring) or (key = #27);
            if key <> #27 then
                begin
                    for iring := last_ring + 1 to actual_last_ring
                        begin
                            fillchar(diop [iring],8*lim1,0);
                            fillchar(ht [iring],8*lim1,0);
                        end;
                    smooth_powers(diop);
                    write_output_files_to_disk;
                end;
        end;                    { not error }
end.
program compute_ball_radius_related_magnification_function;
            {October 13, 1987 by Mart}
const
    last_ring = 28;
    iblock = 2;
    lim = 255;
    lim1 = 256;
    scale = 44.0;
    est_elev_ring_1 = 0.007;
    ball_rad1 = 8.731;
    ref_ball_rad = 7.849;
    ball_rad3 = 6.731;
    file_m1 = '/tables/373_01.mag';
    file_m3 = '/tables/373_03.mag';
    file_g = '/tables848b.tab';
    file_r1 = '/scan/373_01.rng';
    file_r3 = '/scan/373_03.rng';
type
    words = string[80];
    corneal_data = array[0..lim] of real;
    corneal_file = array[1..last_ring] of corneal_data;
    corneal_ptr =   corneal_file;
    short_vec = array [1..2] of real;
    long_vec = array [1..32] of real;
var
    ring1,ring3,camera_distortion,g: corneal_ptr;
    est_rad1,est_rad3,xdotx,xdotm: real;
    ring_fil1,ring_fil3,err_fil,mag_fil1,mag_fil3,out_fil,g_fil:
file;
    mag_const1,mag_const3: array [1..32] of real;
    x: short_vec;
    mag_correction: long_vec;
    key: char;
```

APPENDIX-continued

```
error: matrix_error;
begin
  new(g);
  new(ring1);
  new(ring3);
  new(camera_distortion);
  assign(g_fil,file_g);
  reset(g_fil);
  for iring := 1 to last_ring do
    blockread(g_fil,g [iring],16);
  close(g_fil);
  assign(ring_fil1,file_r1);
  reset(ring_fil1);
  for iring := 1 to last_ring do
    blockread(ring_fil1,ring1 [iring],16);
  close(ring_fil1);
  assign(ring_fil3,file_r3);
  reset(ring_fil3);
  for iring := 1 to last_ring do
    blockread(ring_fil3,ring [iring],16);
  close(ring_fil3);
  assign(mag_fil1,file_m1);
  reset(mag_fil1);
  blockread(mag_fil1,mag_const1,iblock);
  close(mag_fil1);
  assign(mag_fil3,file_m3);
  reset(mag_fil3);
  blockread(mag_fil3,mag_const3,iblock);
  close(mag_fil3);
  for iring := 1 to last_ring do
    begin
      est_rad1 := vector_mean(ring1 [iring]) * g [iring][0];
      est_rad3 := vector_mean(ring3 [iring]) * g [iring][0];
      x[1]:= (est_rad1 - ref_ball_rad) / ref_ball_rad;
      x[2]:= est_rad3 - ref_ball_rad) / ref_ball_rad;
      xdotx := sqr(x[1]) + sqr(x[2]);
      xdotm := x[1] * (mag_const1[iring] - 1.0) +
               x[2] * (mag_const3[iring] - 1);
      mag_correction [iring] := xdotm / xdotx;
      write(mag_correction[iring]:8:6,' ');
    end;
  assign(out_fil,'/tables/mag_corr.tab');
  rewrite(out_fil);
  blockwrite(out_fil,mag_correction,iblock);
  close(out_fil);
end.
```

What is claimed is:

1. The process of mapping a three-dimensional anatomical surface comprising the steps of:

projecting intersecting laser beams at a point on said surface;

exposing said surface to a predetermined illuminated pattern of concentric mires;

storing a two-dimensional video image of said pattern appearing on said surface;

scanning said stored image radially of the image of said mires to detect illumination values corresponding to said pattern;

identifying the two-dimensional coordinates of pixels in said image exhibiting said illumination values;

ascertaining the distance of said pixel coordinates from said point; and processing said pixel coordinate values and said distance to ascertain the third dimensional coordinates for substantially all of said two-dimensional pixel coordinates.

2. The process of claim 1 wherein said processing of said image applies a plurality of coefficients to correct for the reflectivity of said anatomical surface.

3. The process of claim 1 further comprising the steps of:

(a) ascertaining in a two-dimensional sector the coordinates of a plurality of sample-pair points defining a portion of said reflected pattern, (b) identifying the analytic function which produces the least squares error fit to said points lying in said sector.

(c) uniformly incrementally sampling said analytic function for said sector, (d) associating with each sample pair of said sampled function a predetermined sequence of values to define a portion of a three-dimensional surface, (e) incrementally sampling said three-dimensional surface to obtain a sequence of two dimensional points concerning said sequence of two dimensional points defining said reflected pattern, and (f) adjusting the associated third dimensional value to eliminate any discrepancy in said comparing steps.

4. The process of incrementally mappping a three-dimensional anatomical surface comprising the steps of:

projecting intersecting laser beams at a point on said surface;

exposing said surface to a predetermined illuminated pattern of concentric mires;

storing a two-dimensional video image of said pattern appearing on said surface;

incrementally scanning said stored image radially of the image of said mires;

successively multiplying the amplitude of each of said illumination values by a predetermined impulse function to obtain a sequence of amplitude products;

identifying the two-dimension coordinates of pixels in said image giving rise to amplitude products which exceed a predetermined threshold;

ascertaining the distance of said mires to said point; and processing said two-dimensional coordinate values and said distance to ascertain the third dimensional coordinates for each of said two-dimensional coordinates.

5. The method of determining the spherical radius of each of a plurality of points on a corneal refraction surface, comprising the steps of:

(a) projecting a pair of light beams to intersect at a predefined point on the said corneal surface;

(b) presenting a predetermined illuminated target mire pattern toward said surface to cause said pattern to be reflected upon said corneal surface;

(c) acquiring a video image of the reflected pattern;

(d) radially scanning said image to determine the illumination amplitudes of pixels lying along predetermined azimuths in said image passing through said video image of said predefined point;

(e) convolving said illumination amplitudes with a matching filter to determine the polar coordinates of points on said mire pattern appearing in said image;

(f) applying a first plurality of coefficients of correction to correct for the distortion occasioned in acquiring said video image, (g) applying a second coefficient of correction that relates the polar radius of each of said points in said image to a corresponding spherical radius of said cornea; and (h) compensating said spherical radius related by said coefficient for the magnification effects of the cornea under measurement.

6. The method of claim 5 wherein said light beams are low energy laser beams intersecting at said pre-defined point on said optical axis.

7. The method of claim 6 where said positioning step locates said pre-defined point at controlled distance from said target mires.

8. The method of claim 5 wherein said second coefficient of correction is determined by:
sequentially positioning apical surfaces of different spheres of known spherical radius at said point on said optical axis, and
comparing the two-dimensional radii of corresponding mires appearing in the respective images of said different spheres.

9. The method of claim 5 wherein said step of compensating said spherical radius comprises the steps of:
multiplying said spherical radius by a factor, M(x), which relates the magnification effect of a sphere of unknown radius to the magnification effect of a known standard sphere, where M(x) is determined from the solution of:

$$M(x) = 1 + a_1 x + a_2 x^2 + a_3 x^3 + \ldots, \text{ where}$$

$$x = \frac{R_2 - R_{ref}}{R_{ref}}$$

and where $R_2$ is said spherical radius and $R_{ref}$ is the spherical radius of a known standard sphere, both said spheres being sequentially positioned at said point on said optical axis.

10. The method of claim 5 wherein said positioning step includes reflecting a fixation light spot upon said corneal surface.

11. The method of claim 5 wherein said pre-determined mire pattern comprises a plurality of evenly spaced illuminated rings substantially extending from said optical axis to the corneal limbus.

12. The method of claim 5 wherein said first plurality of coefficients of correction are determined by forming quotients of the average measured radius of each of said mires in said image and the plurality of individually measured radii of corresponding ones of said mires in said image.

13. The method of claim 5 wherein said step of convolving includes the step of selecting convolution products exceeding a predetermined threshhold.

* * * * *